US011160977B2

(12) United States Patent
Naveh et al.

(10) Patent No.: US 11,160,977 B2
(45) Date of Patent: Nov. 2, 2021

(54) DELIVERING TUMOR TREATING FIELDS (TTFIELDS) TO THE INFRATENTORIAL BRAIN

(71) Applicant: Novocure Limited, St. Helier (JE)

(72) Inventors: Ariel Naveh, Haifa (IL); Shay Levi, Tel Aviv-Jaffa (IL); Zeev Bomzon, Kiryat Tivon (IL); Eilon Kirson, Ramat Hasharon (IL)

(73) Assignee: Novocure GmbH, Root (CH)

( * ) Notice: Subject to any disclaimer, the term of this patent is extended or adjusted under 35 U.S.C. 154(b) by 160 days.

(21) Appl. No.: 16/120,927

(22) Filed: Sep. 4, 2018

(65) Prior Publication Data

US 2020/0069937 A1 Mar. 5, 2020

(51) Int. Cl.
*A61N 1/36* (2006.01)
*A61N 1/04* (2006.01)
*A61N 1/32* (2006.01)

(52) U.S. Cl.
CPC ....... *A61N 1/36002* (2017.08); *A61N 1/0456* (2013.01); *A61N 1/0476* (2013.01); *A61N 1/323* (2013.01); *A61N 1/36034* (2017.08)

(58) Field of Classification Search
CPC ............ A61N 1/36002; A61N 1/36034; A61N 1/0456
See application file for complete search history.

(56) References Cited

U.S. PATENT DOCUMENTS

| | | | |
|---|---|---|---|
| 6,868,289 B2 | 3/2005 | Palti | |
| 7,016,725 B2 | 3/2006 | Palti | |
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |

(Continued)

*Primary Examiner* — Joseph M Dietrich
(74) *Attorney, Agent, or Firm* — Potomac Law Group, PLLC

(57) ABSTRACT

This application discloses an improved approach for delivering Tumor Treating Fields (TTFields) at a therapeutically effective strength to the infratentorial regions of the brain. A first set of electrode elements is positioned on top of the head and a second set of electrode elements is positioned on the back of the neck. Third and fourth sets of electrode elements are positioned on the lower back right and the lower back left portions of the scalp, respectively. Applying an AC voltage between the first and second sets of electrode elements generates a generally vertical field in the infratentorial regions of the brain; and applying an AC voltage between the third and fourth sets of electrode elements generates a generally horizontal field in those regions.

19 Claims, 6 Drawing Sheets

(56) References Cited

U.S. PATENT DOCUMENTS

| | | |
|---|---|---|
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 2011/0137229 A1* | 6/2011 | Palti .................... A61N 1/40 604/20 |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2018/0333574 A1* | 11/2018 | Pal ................ A61N 1/36034 |

\* cited by examiner

DELIVERING TUMOR TREATING FIELDS (TTFIELDS) TO THE INFRATENTORIAL BRAIN

BACKGROUND

TTFields are low intensity (e.g., 1-4 V/cm) alternating electric fields within the intermediate frequency range (e.g., 100-300 kHz), which may be used, for example, to treat tumors as described in U.S. Pat. No. 7,565,205, which is incorporated herein by reference in its entirety. TTFields therapy is an approved mono-treatment for recurrent glioblastoma (GBM), and an approved combination therapy with chemotherapy for newly diagnosed GBM patients. These alternating electric fields are induced non-invasively by transducer arrays (i.e., arrays of capacitively coupled electrodes) placed directly on the patient's scalp (e.g., using the Novocure Optune™ system), and applying AC voltages between the transducer arrays.

SUMMARY OF THE INVENTION

One aspect of the invention is directed to a first method of treating a tumor located in an infratentorial region of a person's brain. The first method comprises affixing a first set of electrode elements having a first centroid to the person's scalp with the first centroid positioned on top of the person's head; affixing a second set of electrode elements having a second centroid to the back of the person's neck with the second centroid positioned between the person's C2 and C7 vertebrae; affixing a third set of electrode elements having a third centroid to a right half of the person's scalp, with the third centroid positioned posterior with respect to an external opening of the person's right ear canal, and inferior with respect to a midpoint of a glabella of a frontal bone of the person's skull; and affixing a fourth set of electrode elements having a fourth centroid to a left half of the person's scalp, with the fourth centroid positioned posterior with respect to an external opening of the person's left ear canal, and inferior with respect to the midpoint of the glabella of the frontal bone of the person's skull. The first method also comprises repeating, in an alternating sequence (a) applying an alternating voltage between the first set of electrode elements and the second set of electrode elements, and (b) applying an alternating voltage between the third set of electrode elements and the fourth set of electrode elements. The repeating is performed after affixing the first, second, third, and fourth sets of electrode elements.

In some instances of the first method, the third centroid is at least 2 cm posterior with respect to the external opening of the person's right ear canal, and the fourth centroid is at least 2 cm posterior with respect to the external opening of the person's left ear canal. In some instances of the first method, the electrode elements of the first, second, third, and fourth sets are capacitively coupled.

In some instances of the first method, the alternating voltage that is applied between the first set of electrode elements and the second set of electrode elements has a frequency between 100 kHz and 300 kHz, and the alternating voltage that is applied between the third set of electrode elements and the fourth set of electrode elements has a frequency between 100 kHz and 300 kHz.

In some instances of the first method, the first set of electrode elements comprises a plurality of electrode elements wired in parallel, the second set of electrode elements comprises a plurality of electrode elements wired in parallel, the third set of electrode elements comprises a plurality of electrode elements wired in parallel, and the fourth set of electrode elements comprises a plurality of electrode elements wired in parallel.

In some instances of the first method, the first set of electrode elements is affixed with the first centroid positioned between 1 and 3 cm anterior to a vertex of the person's head. In some instances of the first method, the second set of electrode elements is affixed with the second centroid positioned between the person's C3 and C6 vertebrae.

Another aspect of the invention is directed to a second method of treating a tumor located in an infratentorial region of a person's brain. The second method comprises affixing a first set of electrode elements having a first centroid to the person's scalp with the first centroid positioned on top of the person's head; affixing a second set of electrode elements having a second centroid to the back of the person's neck with the second centroid positioned between the person's C2 and C7 vertebrae; affixing a third set of electrode elements having a third centroid to the person's scalp with the third centroid positioned directly to the right of the person's cerebellum; and affixing a fourth set of electrode elements having a fourth centroid to the person's scalp with the fourth centroid positioned directly to the left of the person's cerebellum. The second method also comprises repeating, in an alternating sequence (a) applying an alternating voltage between the first set of electrode elements and the second set of electrode elements, and (b) applying an alternating voltage between the third set of electrode elements and the fourth set of electrode elements. The repeating is performed after affixing the first, second, third, and fourth sets of electrode elements.

In some instances of the second method, the electrode elements of the first, second, third, and fourth sets are capacitively coupled.

In some instances of the second method, the alternating voltage that is applied between the first set of electrode elements and the second set of electrode elements has a frequency between 100 kHz and 300 kHz, and the alternating voltage that is applied between the third set of electrode elements and the fourth set of electrode elements has a frequency between 100 kHz and 300 kHz.

In some instances of the second method, the first set of electrode elements comprises a plurality of electrode elements wired in parallel, the second set of electrode elements comprises a plurality of electrode elements wired in parallel, the third set of electrode elements comprises a plurality of electrode elements wired in parallel, and the fourth set of electrode elements comprises a plurality of electrode elements wired in parallel.

In some instances of the second method, the first set of electrode elements is affixed with the first centroid positioned between 1 and 3 cm anterior to a vertex of the person's head. In some instances of the second method, the second set of electrode elements is affixed with the second centroid positioned between the person's C3 and C6 vertebrae.

Another aspect of the invention is directed to a third method of treating a tumor located in an infratentorial region of a person's brain. The third method comprises affixing a first set of electrode elements having a first centroid to the person's scalp with the first centroid positioned on top of the person's head; and affixing a second set of electrode elements having a second centroid to the back of the person's neck with the second centroid positioned between the person's C2 and C7 vertebrae. The third method also comprises applying an alternating voltage between the first set of electrode elements and the second set of electrode elements. The applying is performed after affixing the first and second sets of electrode elements.

In some instances of the third method, the electrode elements of the first and second sets are capacitively coupled. In these instances, the alternating voltage that is applied between the first set of electrode elements and the second set of electrode elements optionally has a frequency between 100 kHz and 300 kHz.

In some instances of the third method, the electrode elements of the first and second sets are capacitively coupled, the alternating voltage that is applied between the first set of electrode elements and the second set of electrode elements has a frequency between 100 kHz and 300 kHz, the first set of electrode elements comprises a plurality of electrode elements wired in parallel, and the second set of electrode elements comprises a plurality of electrode elements wired in parallel.

In some instances of the third method, the electrode elements of the first and second sets are capacitively coupled, the alternating voltage that is applied between the first set of electrode elements and the second set of electrode elements has a frequency between 100 kHz and 300 kHz, and the first set of electrode elements is affixed with the first centroid positioned between 1 and 3 cm anterior to a vertex of the person's head.

In some instances of the third method, the electrode elements of the first and second sets are capacitively coupled, the alternating voltage that is applied between the first set of electrode elements and the second set of electrode elements has a frequency between 100 kHz and 300 kHz, and the second set of electrode elements is affixed with the second centroid positioned between the person's C3 and C6 vertebrae.

Another aspect of the invention is directed to a first apparatus for treating a tumor located in an infratentorial region of a person's brain. The first apparatus comprises a first set of electrode elements affixed to the person's scalp, having a first centroid positioned on top of the person's head; a second set of electrode elements affixed to the back of the person's neck, having a second centroid positioned between the person's C2 and C7 vertebrae; a third set of electrode elements affixed to a right half of the person's scalp, having a third centroid positioned posterior with respect to an external opening of the person's right ear canal, and inferior with respect to a midpoint of a glabella of a frontal bone of the person's skull; and a fourth set of electrode elements affixed to a left half of the person's scalp, having a fourth centroid positioned posterior with respect to an external opening of the person's left ear canal, and inferior with respect to the midpoint of the glabella of the frontal bone of the person's skull.

In some embodiments of the first apparatus, the electrode elements of the first, second, third, and fourth sets are capacitively coupled.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Pre-clinical experiments suggest that in order for TTFields to exert a therapeutic effect, field intensities should exceed a threshold of about 1 V/cm. And until now, treatment using TTFields has been limited to the supratentorial regions of the brain because all of the prior art layouts for positioning the transducer arrays on a patient's head that could achieve field intensities above 1 V/cm without generating too much heat were layouts for inducing TTFields in the supratentorial regions of the brain.

Figure 1:
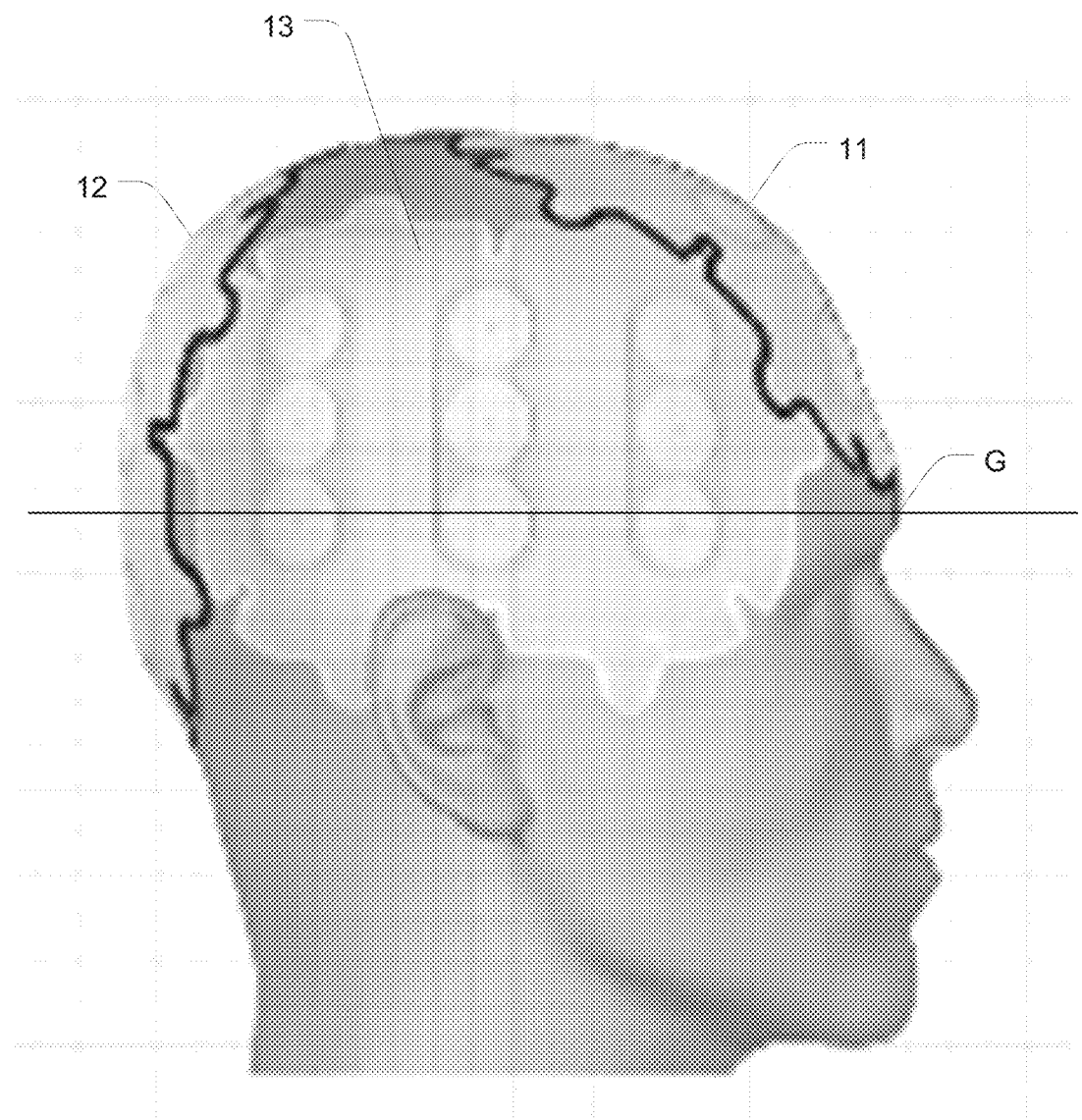
FIG. 1 depicts a prior art layout for positioning transducer arrays on a person's head that is used to induce TTFields in the supratentorial regions of the brain.

FIG. 1 depicts an example of one such prior art layout for positioning the transducer arrays on a patient's head. In this layout, a first transducer arrays 11 is positioned on the patient's forehead, a second transducer array 12 is positioned on the back of the patient's head, a third transducer array 13 is positioned on the right side of the patient's head, and a fourth transducer array (not shown) is positioned on the left side of the patient's head. An AC voltage generator applies an AC voltage (e.g., 200 kHz) between the front and back transducer arrays 11, 12 for a first interval of time (e.g., one second), which generates an electric field with field lines that generally run in a front/back direction. Then, the AC voltage generator applies an AC voltage at the same frequency between the right and left transducer arrays for a second interval of time (e.g., one second), which generates an electric field with field lines that generally run in a right/left direction. The system then repeats this two-step sequence for the duration of the treatment. The layout depicted in FIG. 1 is suitable for achieving field intensities in the supratentorial regions of the brain that exceed 1 V/cm in both the front/back and right/left directions.

This application discloses new approaches for positioning the transducer arrays on a person's head that can achieve field intensities above 1 V/cm in the infratentorial regions of the brain (i.e., the cerebellum and the brainstem).

Figure 2:
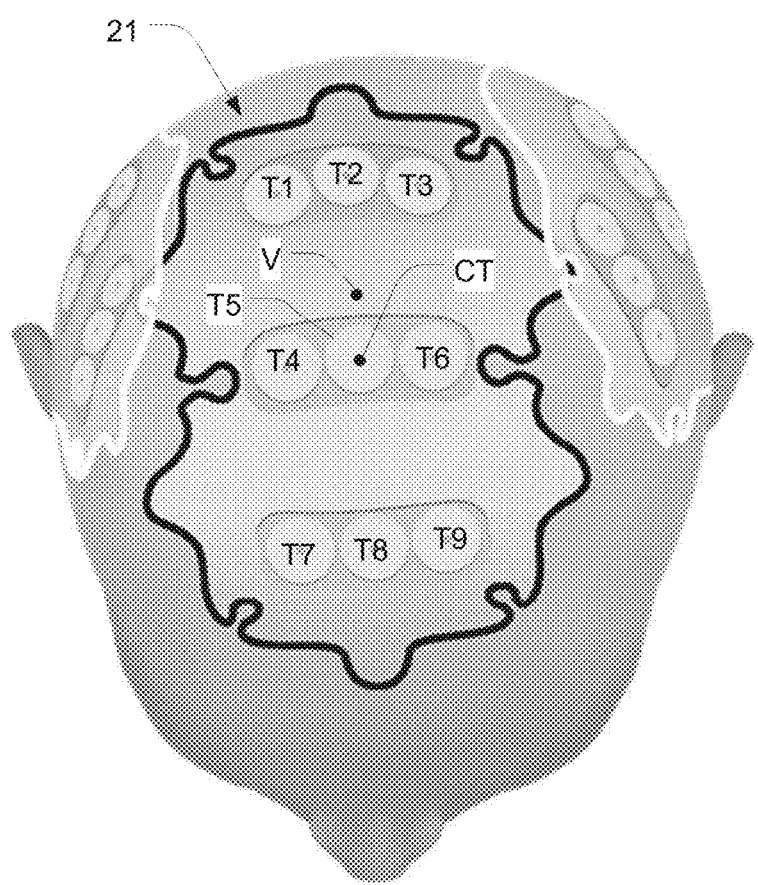
FIG. 2 depicts a layout for positioning transducer arrays on top of a person's head to induce TTFields in the infratentorial regions of the brain.
Figure 3:
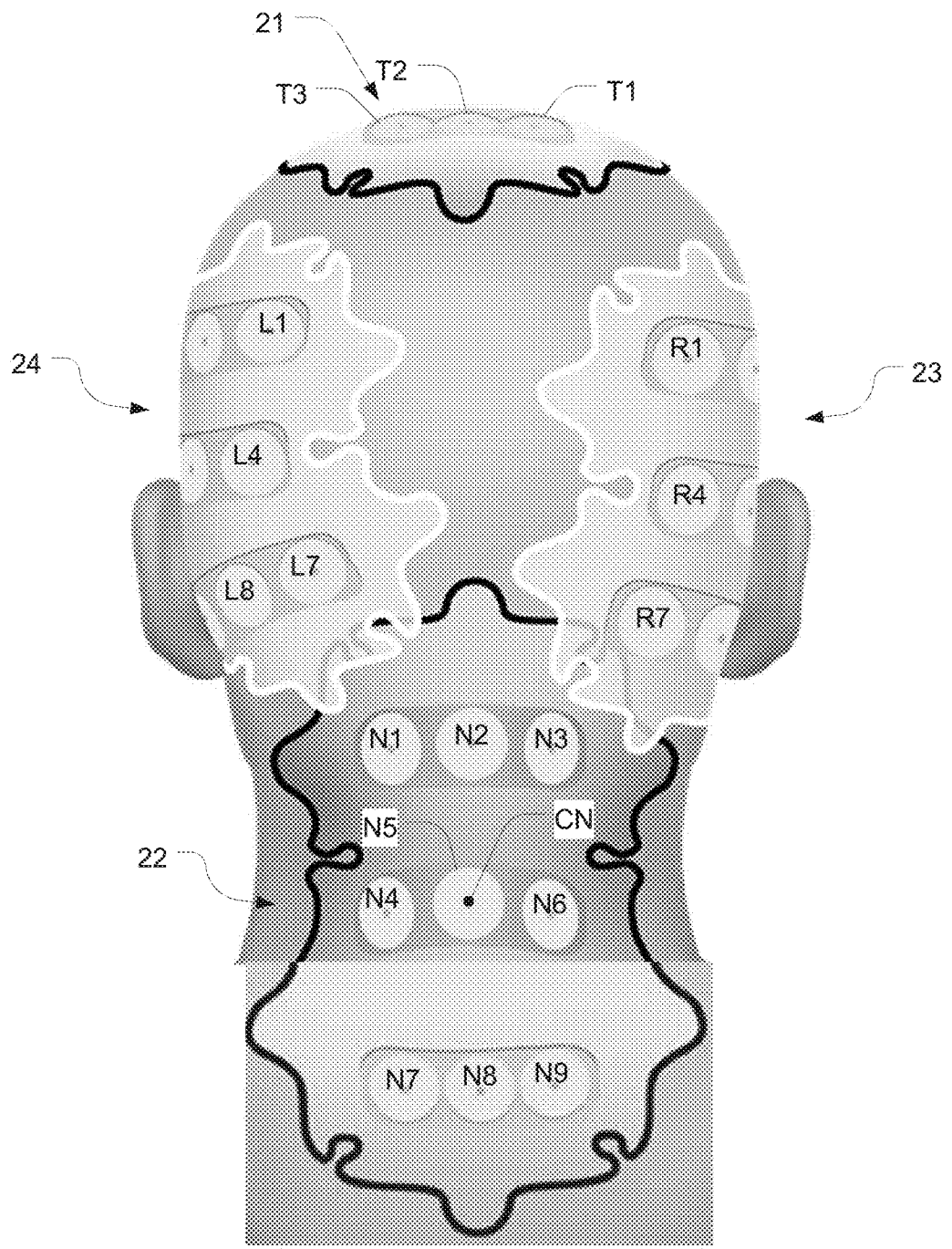
FIG. 3 depicts a layout for positioning transducer arrays on the back of a person's neck to induce TTFields in the infratentorial regions of the brain.
Figure 4:
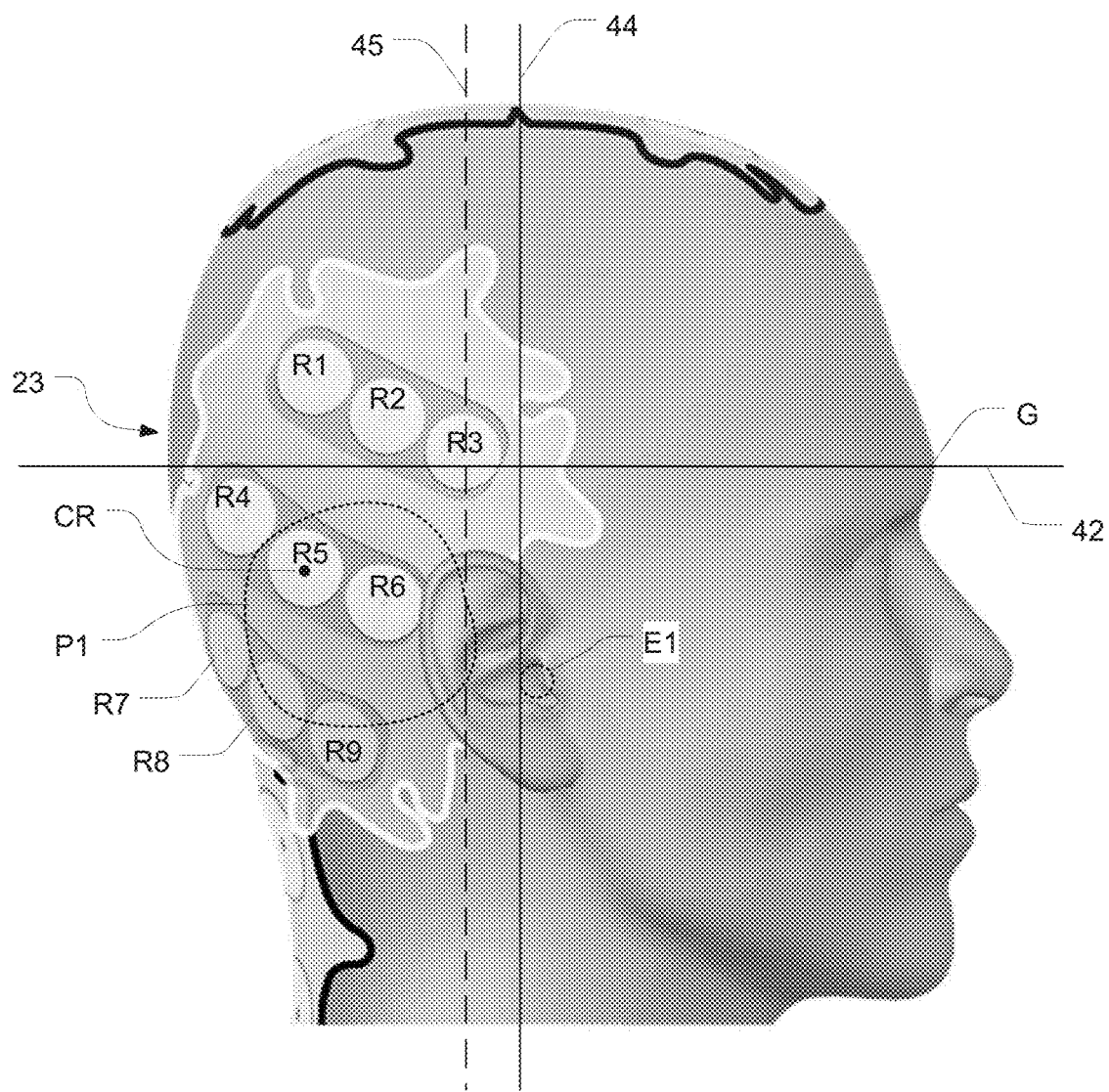
FIG. 4 depicts a layout for positioning transducer arrays on the right side of a person's head to induce TTFields in the infratentorial regions of the brain.
Figure 5:
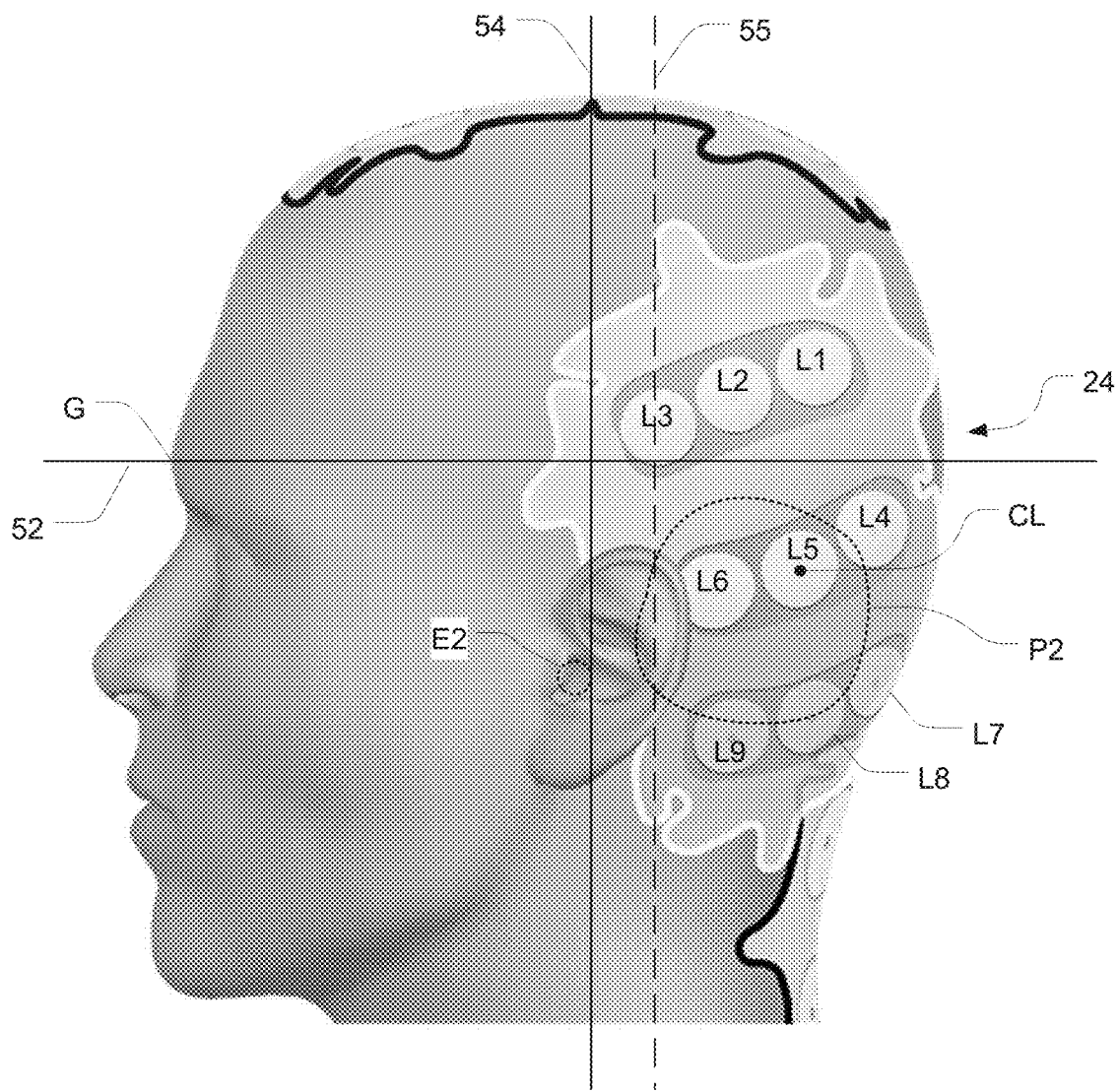
FIG. 5 depicts a layout for positioning transducer arrays on the left side of a person's head to induce TTFields in the infratentorial regions of the brain.

In general terms, a first set of electrode elements is positioned on top of the person's head (as best seen in FIG. 2); a second set of electrode elements is positioned on the back of the person's neck (as best seen in FIG. 3); a third set of electrode elements is positioned on the lower back right portion of the person's scalp (as best seen in FIG. 4); and a fourth set of electrode elements is positioned on the lower back left portion of the person's scalp (as best seen in FIG. 5).

To be more precise, in some embodiments, the first set 21 of electrode elements T1-T9 is affixed to the person's scalp with its centroid CT positioned on top of the person's head (as best seen in FIG. 2); The second set 22 of electrode elements N1-N9 is affixed to the back of the person's neck with its centroid CN positioned between the person's C2 and C7 vertebrae (as best seen in FIG. 3); The third set 23 of electrode elements R1-R9 is affixed to a right half of the person's scalp, with its centroid CR positioned posterior with respect to an external opening E1 of the person's right ear canal (i.e., posterior to the vertical line 44 in FIG. 4), and inferior with respect to a midpoint of a glabella G of a frontal bone of the person's skull (i.e., inferior to the horizontal line 42 in FIG. 4); And the fourth set 24 of electrode elements L1-L9 is affixed to a left half of the person's scalp, with its centroid CL positioned posterior with respect to an external opening E2 of the person's left ear canal (i.e., posterior to the vertical line 54 in FIG. 5), and inferior with respect to the midpoint of the glabella G of the frontal bone of the person's skull (i.e., inferior to the horizontal line 52 in FIG. 5). Optionally, in these embodiments, the third and fourth centroids may be positioned at least 2 cm posterior with respect to the external opening of the person's right and left ear canals, respectively (i.e., posterior to the vertical lines 45, 55 in FIGS. 4 and 5, respectively).

In some embodiments, the first set 21 of electrode elements T1-T9 is affixed to the person's scalp with its centroid CT positioned on top of the person's head (as best seen in FIG. 2); The second set 22 of electrode elements N1-N9 is affixed to the back of the person's neck with its centroid CN positioned between the person's C2 and C7 vertebrae (as best seen in FIG. 3); The third set 23 of electrode elements R1-R9 is affixed to the person's scalp with its centroid CR positioned directly to the right of the person's cerebellum (as best seen in FIG. 4); And the fourth set 24 of electrode elements L1-L9 is affixed to the person's scalp with its centroid CL positioned directly to the left of the person's cerebellum (as best seen in FIG. 5). As used herein "directly to the right" refers to a projection of the cerebellum in a direction that is perpendicular to the sagittal plane onto the right side of a person's scalp, as denoted by the dashed line P1 in FIG. 4. So the centroid CR of the third set of electrodes will be positioned at a spot on the scalp that lies within the dashed line P1 in FIG. 4. And "directly to the left" refers to a projection of the cerebellum in a direction that is perpendicular to the sagittal plane onto the left side of the person's scalp, as denoted by the dashed line P2 in FIG. 5. So the centroid CL of the fourth set of electrodes will be positioned at a spot on the scalp that lies within the dashed line P2 in FIG. 5.

Note that in the embodiments depicted in FIGS. 2-5, each set 21-24 of electrode elements is configured as a 3×3 array of individual electrode element discs. As a result, in these embodiments, the centroid of the respective set 21-24 will coincide with the center of the center disc. But in alternative embodiments, each set of electrode elements may include a different number of electrode elements. For example, a given set of electrode elements may be configured as a 2×2 array of individual electrode element discs. In this situation, the centroid could be in a region that is located between all four disks. In other alternative embodiments, a given set of electrode elements may include only a single electrode element disc. In this situation, the centroid would coincide with the center of that single disc.

All four sets of electrode elements are preferably capacitively coupled to the person's body.

After affixing the first, second, third, and fourth sets of electrode elements as described above for the respective embodiments, the following steps are repeated in an alternating sequence: (a) applying an alternating voltage between the first set of electrode elements and the second set of electrode elements, and (b) applying an alternating voltage between the third set of electrode elements and the fourth set of electrode elements. In some embodiments, the frequency of these alternating voltages is between 100 kHz and 300 kHz.

Optionally, in the embodiments described above, the first set of electrode elements may be affixed so that the first centroid CT is positioned between 1 and 3 cm anterior to the vertex V of the person's head, as best seen in FIG. 2.

Optionally, in the embodiments described above, the second set of electrode elements may be affixed so that the second centroid is positioned between the person's C4 and C5 vertebrae, or between the person's C3 and C6 vertebrae.

Numerical simulations were run to examine the field intensity distribution in the infratentorial region of the brain when the array layout depicted in FIGS. 2-5 is used to deliver TTFields. The simulations were performed using a highly detailed realistic computational head model of a 40+ year old male developed from a set of high resolution (1×1×1 mm) MRIs. To develop the model, the MRI set was segmented into 6 components including Scalp, Skull, Grey Matter, White Matter, Cerebro-spinal fluid (CSF) and air. Dielectric properties were assigned to the various components according to values previously reported in the literature. See, e.g., Wenger et. al, Phys. Med. Biol. 60 7339-7357 (2015), which is incorporated herein by reference in its entirety.

Models of transducer arrays (Novocure part no. INE9000 and INE9000W) were placed on the skin of the phantom at the positions depicted in FIGS. 2-5. Simulated TTFields were generated within the model brain by delivering a simulated current of 2 A peak to peak between the first and second sets of electrode elements. Simulated TTFields were also generated within the model brain by delivering a simulated current of 2 A peak to peak between the third and fourth sets of electrode elements. The model was solved using a commercial numerical solver. Because the field is delivered to each pair of arrays sequentially, field calculations for each pair of arrays were performed separately.

To analyze the field intensity distribution in the various regions of the brain the brain was divided into five regions: (1) the infratentorial brain, including the brain stem and cerebellum; (2) quarter 1—the supratentorial right anterior region; (3) quarter 2—the supratentorial left anterior region; (4) quarter 3—the supratentorial right posterior region; and (5) quarter 4—the supratentorial left posterior region. The field intensities within each region were analyzed.

Figure 6:
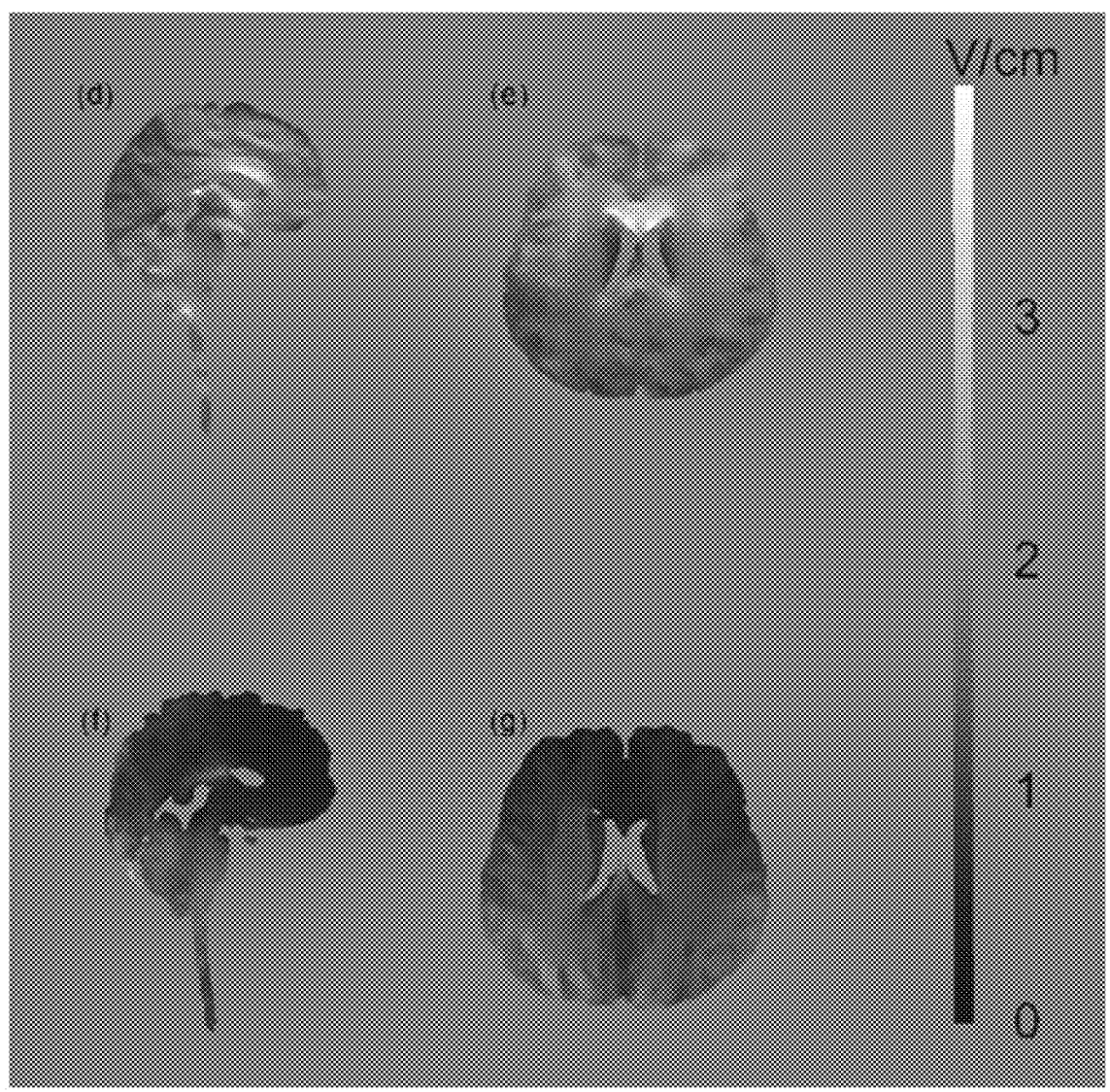
FIG. 6 shows the field distribution in axial and sagittal slices through a computational phantom model when delivering TTFields using the array configuration of FIGS. 2-5

FIG. 6 shows the field distribution in axial and sagittal slices through the computational phantom model when delivering TTFields using the array configuration described above in connection with FIGS. 2-5. The maps show the calculated field intensity of a sagittal slice (d) and an axial slice (e) through the brain generated when a 200 kHz AC voltage was applied between the first (top) and second (neck) sets of electrode elements. They also show the calculated field intensity of a sagittal slice (f) and an axial slice (g) through the brain generated when a 200 kHz AC voltage was applied between the third (right) and fourth (left) sets of electrode elements.

When the AC voltage was applied between the first and second sets of electrode elements, the delivered field intensity was above 1.1 V/cm to over 95% of the volume of the infratentorial brain, with an average field intensity of 1.7 V/cm and a maximal intensity of above 2.3 V/cm within this region. Average field intensities throughout the supratentorial brain exceeded 1.5 V/cm.

When the AC voltage was applied between the third and fourth sets of electrode elements, the delivered field intensity was above 1 V/cm in over 95% of the infratentorial brain. The average intensity within this region is 2 V/cm, with maximal intensities above 2.8 V/cm. Mean field intensities in the supratentorial posterior regions of the brain exceeded 1.4 V/cm, and in the supratentorial anterior regions mean field intensities approached 0.8 V/cm.

This shows that the layouts for the various sets of electrode elements described herein can be used to deliver TTFields at therapeutically effective levels (i.e., greater than 1 V/cm) in two roughly perpendicular directions to the infratentorial brain (i.e., throughout the cerebellum and brain stem), as well as to large regions of the supratentorial brain.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of treating a tumor located in an infratentorial region of a person's brain, the method comprising:
   affixing a first set of electrode elements having a first centroid to the person's scalp with the first centroid positioned on top of the person's head;
   affixing a second set of electrode elements having a second centroid to the back of the person's neck with the second centroid positioned between the person's C2 and C7 vertebrae;
   affixing a third set of electrode elements having a third centroid to a right half of the person's scalp, with the third centroid positioned posterior with respect to an external opening of the person's right ear canal, and inferior with respect to a midpoint of a glabella of a frontal bone of the person's skull;
   affixing a fourth set of electrode elements having a fourth centroid to a left half of the person's scalp, with the fourth centroid positioned posterior with respect to an external opening of the person's left ear canal, and inferior with respect to the midpoint of the glabella of the frontal bone of the person's skull; and
   repeating, in an alternating sequence (a) applying an alternating voltage between the first set of electrode elements and the second set of electrode elements, and (b) applying an alternating voltage between the third set of electrode elements and the fourth set of electrode elements,
   wherein the repeating is performed after affixing the first, second, third, and fourth sets of electrode elements, and
   wherein an electric field with an intensity of at least 1 V/cm is induced in at least a portion of the infratentorial region of the person's brain during the repeating step.

2. The method of claim 1, wherein the third centroid is at least 2 cm posterior with respect to the external opening of the person's right ear canal, and wherein the fourth centroid is at least 2 cm posterior with respect to the external opening of the person's left ear canal.

3. The method of claim 1, wherein the electrode elements of the first, second, third, and fourth sets are capacitively coupled.

4. The method of claim 1, wherein the alternating voltage that is applied between the first set of electrode elements and the second set of electrode elements has a frequency between 100 kHz and 300 kHz, and wherein the alternating voltage that is applied between the third set of electrode elements and the fourth set of electrode elements has a frequency between 100 kHz and 300 kHz.

5. The method of claim 1, wherein the first set of electrode elements comprises a plurality of electrode elements wired in parallel, the second set of electrode elements comprises a plurality of electrode elements wired in parallel, the third set of electrode elements comprises a plurality of electrode elements wired in parallel, and the fourth set of electrode elements comprises a plurality of electrode elements wired in parallel.

6. The method of claim 1, wherein the first set of electrode elements is affixed with the first centroid positioned between 1 and 3 cm anterior to a vertex of the person's head.

7. The method of claim 1, wherein the second set of electrode elements is affixed with the second centroid positioned between the person's C3 and C6 vertebrae.

8. A method of treating a tumor located in an infratentorial region of a person's brain, the method comprising:
   affixing a first set of electrode elements having a first centroid to the person's scalp with the first centroid positioned on top of the person's head;
   affixing a second set of electrode elements having a second centroid to the back of the person's neck with the second centroid positioned between the person's C2 and C7 vertebrae;
   affixing a third set of electrode elements having a third centroid to the person's scalp with the third centroid positioned directly to the right of the person's cerebellum;
   affixing a fourth set of electrode elements having a fourth centroid to the person's scalp with the fourth centroid positioned directly to the left of the person's cerebellum; and
   repeating, in an alternating sequence (a) applying an alternating voltage between the first set of electrode elements and the second set of electrode elements, and (b) applying an alternating voltage between the third set of electrode elements and the fourth set of electrode elements,
   wherein the repeating is performed after affixing the first, second, third, and fourth sets of electrode elements, and
   wherein an electric field with an intensity of at least 1 V/cm is induced in at least a portion of the infratentorial region of the person's brain during the repeating step.

9. The method of claim 8, wherein the electrode elements of the first and second sets are capacitively coupled.

10. The method of claim 9, wherein the alternating voltage that is applied between the first set of electrode elements and the second set of electrode elements has a frequency between 100 kHz and 300 kHz.

11. The method of claim 10, wherein the first set of electrode elements comprises a plurality of electrode elements wired in parallel, and the second set of electrode elements comprises a plurality of electrode elements wired in parallel.

12. The method of claim 10, wherein the first set of electrode elements is affixed with the first centroid positioned between 1 and 3 cm anterior to a vertex of the person's head.

13. The method of claim 10, wherein the second set of electrode elements is affixed with the second centroid positioned between the person's C3 and C6 vertebrae.

14. A method of treating a tumor located in an infratentorial region of a person's brain, the method comprising:
   affixing a first set of electrode elements having a first centroid to the person's scalp with the first centroid positioned on top of the person's head;

affixing a second set of electrode elements having a second centroid to the back of the person's neck with the second centroid positioned between the person's C2 and C7 vertebrae; and applying an alternating voltage between the first set of electrode elements and the second set of electrode elements, wherein the applying is performed after affixing the first and second sets of electrode elements, and wherein an electric field with an intensity of at least 1 V/cm is induced in at least a portion of the infratentorial region of the person's brain during the repeating step.

15. The method of claim 14, wherein the electrode elements of the first and second sets are capacitively coupled.

16. The method of claim 15, wherein the alternating voltage that is applied between the first set of electrode elements and the second set of electrode elements has a frequency between 100 kHz and 300 kHz.

17. The method of claim 16, wherein the first set of electrode elements comprises a plurality of electrode elements wired in parallel, and the second set of electrode elements comprises a plurality of electrode elements wired in parallel.

18. The method of claim 16, wherein the first set of electrode elements is affixed with the first centroid positioned between 1 and 3 cm anterior to a vertex of the person's head.

19. The method of claim 16, wherein the second set of electrode elements is affixed with the second centroid positioned between the person's C3 and C6 vertebrae.

* * * * *